United States Patent [19]

Langham

[11] 4,275,074
[45] Jun. 23, 1981

[54] CATECHOLAMINE TREATMENT OF OCULAR HYPERTENSION

[75] Inventor: Maurice E. Langham, Lutherville, Md.

[73] Assignee: Graham J. Dobbie, Chicago, Ill. ; a part interest

[21] Appl. No.: 19,037

[22] Filed: Mar. 9, 1979

[51] Int. Cl.³ ............... A61K 31/365; A61K 31/135; A61K 31/22; A61K 31/225

[52] U.S. Cl. .................................. 424/280; 424/311; 424/313; 424/330

[58] Field of Search ............... 424/330, 324, 311, 280

[56] References Cited

U.S. PATENT DOCUMENTS

| | | | |
|---|---|---|---|
| 3,657,244 | 4/1972 | Mentrup et al. | 424/330 |
| 3,705,233 | 12/1972 | Lunts et al. | 424/45 |
| 3,732,300 | 5/1973 | Lunts et al. | 424/324 |
| 3,808,317 | 4/1974 | Hecht et al. | 424/175 |
| 3,809,714 | 5/1974 | Hussain et al. | 424/311 |
| 3,839,584 | 10/1974 | Hussain et al. | 424/311 |
| 3,868,461 | 2/1975 | Hussain et al. | 424/311 |
| 3,937,838 | 2/1976 | Wetlerlin et al. | 424/311 |

OTHER PUBLICATIONS

Lewis's Pharmacology–Crossland–4th ed., 1970, pp. 381–382 and 386–387.

*Primary Examiner*—Douglas W. Robinson

[57] ABSTRACT

Ocular hypertension can be treated by the topical administration of ophthalmic compositions that contain as the active ingredient an α-methyl derivative of epinephrine or norepinephrine.

18 Claims, 1 Drawing Figure

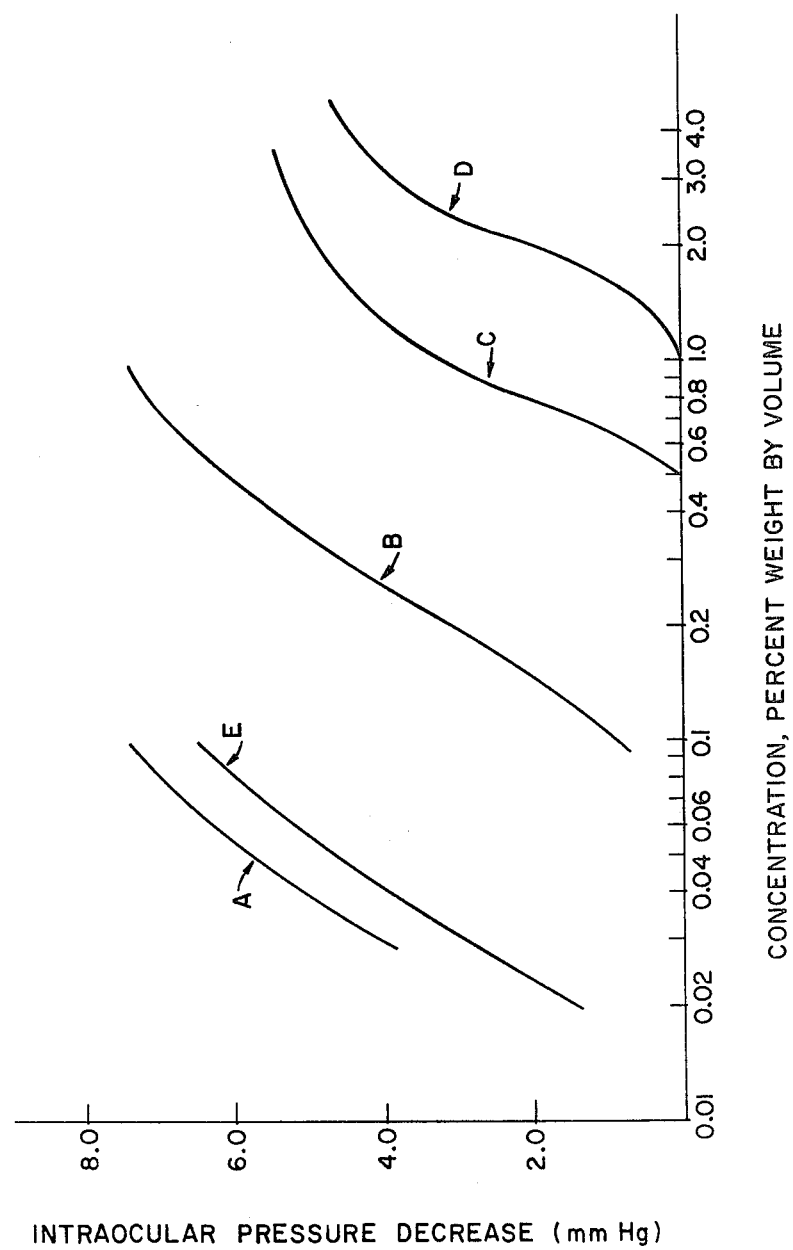

CATECHOLAMINE TREATMENT OF OCULAR HYPERTENSION

BACKGROUND OF THE INVENTION

1. Field of the Invention

The present invention relates to the treatment of ocular hypertension encountered in patients suffering from glaucoma or other ocular disorders. More particularly, this invention relates to a composition and method for effectively lowering mammalian intraocular pressure.

2. Description of the Prior Art

Increased intraocular tension is caused by a disruption of the normal mechanisms regulating the pressure within the eye of a mammal. A great deal of progress has recently been made in understanding these mechanisms. It is now well established that aqueous humor drains from the eye through a sieve-like barrier into a complex network of small vessels. Ocular hypertension is directly related to rate of secretion of aqueous humor into the eye and to outflow resistance of the drainage channels, although the mechanisms of these phenomena remain to be elucidated.

One of the diseases of the mammalian eye characterized by increased intraocular tension is glaucoma. Manifestations of glaucoma include hardening of the globe, excavation of the optic disc and restriction of the field of vision. Glaucoma causes blindness and, in Western man, indeed, is the leading cause of blindness.

The presently available methods of therapy for the treatment of glaucoma consist mainly of the administration of miotics, the adrenergic drug epinephrine, carbonic anhydrase inhibitors, and/or surgery. Surgery usually is reserved for the treatment of the less common, acute congestive form of glaucoma and for those cases of chronic open-angle glaucoma that do not respond to drug therapy. The carbonic anhydrase inhibitors seldome suffice as the sole means of therapy and are used in conjunction with miotics in the therapy of chronic glaucoma and as a preparatory measure to reduce intraocular pressure prior to surgery.

At the present, the mainstay of glaucoma therapy is the topical administration of miotics. The most commonly employed miotic is pilocarpine. This drug has certain disadvantages, namely, the need for frequent administration, usually around the clock instillation. In addition, pilocarpine causes a "pin point" pupil with associated restriction of vision. Incidentally, the loss of motility of the iris, as manifested by the "pin point" pupil, when miotics are employed is a pronounced disadvantage of all drugs presently used in the treatment of glaucoma. In addition, tachyphylaxis or tolerance to the drug is not uncommon, and increasingly stronger solutions must be used for continued therapy. Often, tolerance develops even to the uppermost dose level available.

In recent years the adrenergic drug epinephrine has been used as a valuable alternate or substitute to the miotics. It has been of especial value in the younger glaucoma patient, where the spasm of the ciliary muscle induced by miotic treatment is particularly disabling. Epinephrine is usually applied twice a day either with or without other drugs. Unfortunately, the drug has to be used in relatively high concentrations, has a mydriatic effect, and toleration of the ocular tissues to epinephrine usually is approximately two years. Epinephrine also induces undesirable side effects of congestive hyperemia of the conjunctival vessels due, principally, to its β adrenoceptor agonist activity. U.S. Pat. No. 3,809,714 to Hussain et al. discloses the activity of dipivalyl epinephrine for the treatment of glaucoma; however, this particular compound also elicits a mydriatic (pupil dilation) response.

Mydriasis is particularly undesirable in the treatment of narrow-angle glaucoma since known mydriatic compounds such as epinphrine, nonpinephrine and dipivalyl epinephrine provoke occlusion of the irido-corneal angle with a resulting increased resistance to aqueous flow and a consequent rise in ocular tension in spite of a reduced aqueous flow.

Therefore, there is an outstanding need for new therapeutic agents and, indeed, new approaches which can be employed in the treatment of ocular hypertension, particularly in cases of glaucoma, without the attendant disadvantages of the presently available measures. The present invention provides a new pharmacological approach to the treatment of ocular hypertension utilizing α-methyl derivatives of epinephrine and norepinephrine that have been found to exhibit an unexpectedly high activity in reducing mammalian intraocular pressure without eliciting attendant undesirable pupillary and accommodative responses at concentrations effective in reducing intraocular pressures, and that are not substrates for monoamine oxidase and consequently are not readily destroyed after administration.

The unexpected nature of the present invention is further underscored by literature reports that such α-methyl derivatives are relatively inactive in other tissues as compared to epinephrine and norepinephrine, such as, for example, J. Pharmacol. Exp. Therap. 161:279-295 (1968); J. Pharm. Pharmac., 1969, 21, Suppl., 199S-205S; and JADA, 92:748-750 (1976). In Annals of Ophthalmology, 3, No. 3, 282 (March 1971), it is reported that the α-methyl derivatives of epinephrine and norepinephrine (dioxyephedrine and nordefrin, respectively) are inactive in lowering intraocular pressure.

SUMMARY OF THE INVENTION

The present invention contemplates ophthalmic compositions effective for lowering mammalian intraocular tension and containing as an active ingredient α-methyl epinephrine, α-methyl norepinephrine, or an aliphatic ester thereof and a method of treatment for ocular hypertension by topically applying to the eye of the mammal in need of such treatment the aforementioned compositions.

In particular, the present compositions in unit dosage form contain as an active ingredient about 0.01 to about 5 milligrams, preferably about 0.02 to about 2 milligrams, of a catecholamine which is a member of the group consisting of the compounds represented by the general formula

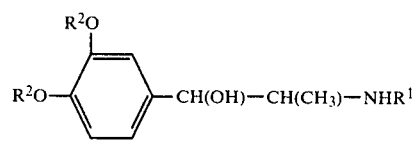

wherein $R^1$ can be hydrogen or methyl and wherein $R^2$ can be hydrogen or an acyl moiety containing 1 to 8 carbon atoms, inclusive. The foregoing compounds can be used in a free base form or as pharmacologically acceptable acid addition salts. The present compositions also contain a diluent amount of an ophthalmic vehicle.

The foregoing active ingredients are effective in lowering mammalian intraocular pressure, when administered in an appropriate dosage form, either singly or in combination with other known anti-glaucomatous drugs. Relatively low concentrations of the aforementioned α-methyl derivatives produce a long-lasting decrease of intraocular pressure in the mammalian eye with substantially no dilation of the pupil. Moreover, these α-methyl derivatives of epinephrine and norepinephrine are effective in decreasing the intraocular pressure at much lower concentrations than epinephrine and norepinephrine.

BRIEF DESCRIPTION OF DRAWING

The sole FIGURE shows the dose response curves for dipivalyl α-methyl norepinephrine, α-methyl norepinephrine, epinephrine, norepinephrine and dipivalyl α-methyl epinephrine.

DETAILED DESCRIPTION OF THE PREFERRED EMBODIMENTS

The compositions of my invention can contain as the active ingredient α-methyl norepinephrine, α-methyl epinephrine, or acylated derivatives (esters) of these compounds in a conventional ophthalmic vehicle which serves as a diluent for effective unit dosage forms. The active ingredients are known compounds and some are commercially avaiable under the designations Cobefrin, Nordefrin, Corbasil, and Carbocaine. Preparation of compounds contemplated as active ingredients for the purposes of the present invention is also disclosed in U.S. Pat. No. 3,904,671 to Minatoya et al.

The acylated derivatives of α-methyl epinephrine and α-methyl norepinephrine may be hydrolyzed to α-methyl epinephrine and α-methyl norepinephrine while in the mammalian eye; however, the presence of the ester group or groups on the acylated derivatives enhances the chemical stability and the lipoid solubility of these compounds, and thus facilitates the transport thereof into the eye.

Illustrative of the acyl moieties that can be present are formyl, acetyl, propionyl, butyryl, isobutyryl, valeryl, isovaleryl, pivaloyl, caproyl, capryloyl, and the like.

To prepare the acylated derivatives of the compounds shown in the above formula, the 3—OH and 4—OH groups of the compounds themselves, or of their precursors, can be esterified by acylating agents such as anhydrides, mixed anhydrides, or the chloride of the appropriate alkanoic acid using conventional acylation conditions.

The compounds herein contemplated as active ingredients have two assymmetric carbon atoms and thus each compound can exist in four epimeric forms, i.e., as the (−)erythro, (+)erythro, (−)threo, (+)threo stereoisomer. For the purposes of the present invention the particular stereoisomers can be used individually or as racemic mixtures.

The foregoing compounds can exist and can be used in the non-protonated or free base form as well as in the protonated or acid addition salt form, depending on the pH of the environment therefor.

Physiologically tolerable acid addition salts of the foregoing compounds can be prepared by the neutralization of the free base form with an appropriate amount of an organic or inorganic acid, examples of which are hydrochloric, hydrobromic, phosphoric, acetic, lactic, salicylic, glycolic, ascorbic, succinic, tartaric, maleic, malic, pamoic, citric, and the like. The preferred acid addition salts for the present purposes are the hydrochlorides, ascorbates, and maleates.

The neutralization can be carried out by a variety or procedures known to the art to be generally useful for the preparation of amine acid addition salts. The choice of the most suitable procedure will depend on a variety of factors including convenience of operation, economic considerations, and particularly the solubility characteristics of the particular free base, the acid, and the acid addition salt.

For example, if the acid is soluble in water, the free base can be dissolved in water containing an equivalent amount of the acid, and thereafter, the water can be removed by evaporation; in some instances, the salt precipitates from the aqueous solution, particularly when cooled, and evaporation is not necessary. If the acid is soluble in a relatively non-polar solvent, for example, diethyl ether or diisopropyl ether, separate solutions of the acid and free base in such a solvent can be mixed in equivalent amounts, whereupon the acid addition salt will usually precipitate because of its relatively low solubility in the non-polar solvent. Alternatively, the free base can be mixed with an equivalent amount of the acid in the presence of a solvent of moderate polarity, for example, a lower alkanol, a lower alkanone, or a loweralkyl ester of a lower alkanoic acid. Examples of these solvents are ethanol, acetone, and ethyl acetate, respectively. Subsequent admixture of the resulting solution of acid addition salt with a solvent of relatively low polarity, for example, diethyl ether or hexane, will usually cause precipitation of the acid addition salt. The formation of acid addition salts can also be utilized for upgrading the free bases prior to formulation, if necessary.

The compositions of the present invention can be administered topically to the eye in unit dosage form, as ophthalmic solutions (including physiological saline), or as ophthalmic ointments, creams, gels, or dispersions. Typical ointment bases suitable for this purpose include white petrolatum and mineral oil or liquid petrolatum. Slow release polymers or depo systems incorporating the described α-methyl derivatives of epinephrine and/or norepinephrine can also be employed if desired.

The term "unit dosage form" as used in the specification and claims refers to physically discrete units suitable as unitary dosages for humans and animals, each unit containing a predetermined quantity of active material calculated to produce the desired therapeutic effect in association with the required diluent, i.e., carrier, or vehicle. The specifications for the novel unit dosage forms of this invention are dictated by and are directly dependent on (a) the unique characteristics of the active material and the particular therapeutic effect to be achieved, and (b) the limitations inherent in the art of compounding such active material for therapeutic use in humans and animals, as disclosed in detail in the specification, these being features of the present invention. The unit dosage forms can be manually delivered to the eye as drops, or by suitable microdrop or spray devices typically providing a metered dose of medication.

The amount of active ingredient that is to be administered depends on the age, weight of the patient, the particular condition to be treated, the frequency of administration, and the like. The human dose can range from about 0.01 to about 5 milligrams daily given as a single dose or in 3 or 4 divided doses. Preferably, the daily adult human dose is from about 0.02 to about 2 milligrams. Veterinary dosages will correspond to human dosages with the amounts administered being in proportion to the weight of the animal as compared to adult humans.

Generally, the concentration of the active ingredient in the solution is within the range of 0.001 to 0.15 percent weight by volume. Higher concentrations of solutions, as for example, from about 0.2 to about 0.5 percent weight by volume. as well as lower concentrations can be employed (as for example, in a solution in combination with a miotic, e.g., pilocarpine, or with a sympathomimetic amine), provided that the ultimate solution concentrations of the present α-methyl derivatives of epinephrine or norepinephrine together with the exogenous sympathomimetic amines and the miotic are effective in lowering intraocular pressure and are non-irritating.

In the treatment of glaucoma in man, the antiglaucoma compositions of my invention can be initially administered in unit dosage form, i.e., dropwise, three times daily. After the patient has responded, as determined by a sustained lowering of intraocular pressure and significant alleviation of the manifestations of glaucoma, the daily regimen may be reduced to once a day or once every other day or less, as a maintenance dose for continued effect.

As stated hereinabove, the concentration of active ingredient in the present compositions may be varied. It is necessary, however, that the active ingredient is present in an amount such that a suitable dosage will be delivered to the patient. While several unit dosage forms may be administered at about the same time, administration at appropriate periodic intervals to achieve the desired effect is preferable. Activity increases with concentration of the active ingredient in the unit dose, and in general, it has been found to be desirable to maintain unit dosage concentrations below that level at which any systemic action due to the α-methyl derivative present is observable. Such concentrations generally fall within the above-described ranges; however, it is to be understood that these general ranges may be modified in certain instances to suit the needs and responses of an individual patient. Therefore, any dose which will produce the desired effect without irritation, and furthermore, falls below the toxic dose, in most instances below the $LD_{50}$ dose of the particular α-methyl derivative present, can be employed.

For the present purposes sterile physiological saline is a suitable vehicle. Other suitable ophthalmic vehicles are well known in the art and are fully described in such standard reference works as *Remington's Pharmaceutical Sciences,* Martin and Cook, Mack Publishing Co., Easton, Pa., 13th edition (1965). The following is a suitable example. (The percentages in the following examples refer to a percent weight by volume.)

| STERILE VEHICLE | |
|---|---|
| Ingredient | Percent w/v |
| Oxine sulfate | 0.01 |
| Sodium bisulfite | 0.3 |
| Phenylmercuric acetate | 0.002 |
| Sodium hydroxide or hydrochloric acid | |
| to pH 3.5–6 | |
| Water, q.s. | |

In the foregoing composition, the oxine sulfate (8-hydroxy-quinolone sulfate) and the sodium bisulfite act as antioxidants and the concentration thereof can vary tenfold (the former up to about 0.1 percent, and the latter down to about 0.03 percent). In addition to these specific antioxidants, any ophthalmic antioxidant can be employed. These are more fully described in Remington (supra).

Phenyl mercuric acetate is employed as a preservative. Any preservative suitable for ophthalmic formulation such as those described in Remington (supra) can be employed. A pH range from about 3.5–8 can be employed, although a pH value within the physiological range is preferred. When employing a buffered system, it is preferred to utilize a pH of about 6.0 to about 8. With a buffered system, pH is conventionally adjusted by adjusting the concentration and, thereupon, altering the ratio of the buffered tonicity so as to maintain an isotonic solution. Although buffers can be used at varying pH, when pH is less than 6.0, sodium hydroxide or hydrochloric acid can conveniently be employed to adjust the pH. When using a buffered system, it is preferred to adjust the range to that of the physiological pH range of about 6 to 7.5 or 8. U.S. Pat. No,. 3,149,035 to Riegelman sets forth additional specific suitable sterile vehicles that can be employed in formulating the compositions of this invention.

The pH of the foregoing sterile vehicle can be adjusted using base or acid. Also, standard buffering agents such as those described in Remington (supra) or in the *Merck Index,* 9th ed., page Misc. 97, (1976), so long as these buffering agents are suitable for an opthalmic formulation, can be utilized.

Typical formulations effective for lowering mammalian intraocular tension are set forth hereinbelow:

| FORMULATION 1 | |
|---|---|
| Ingredient | Percent w/v |
| (-)erythro-α-methyl epinephrine | 0.05 |
| Oxine sulfate | 0.01 |
| Sodium bisulfite | 0.3 |
| Boric acid | 0.8 |
| Sodium borate | 0.6 |
| Phenylmercuric acetate | 0.002 |
| Water q.s. | |

| FORMULATION II | |
|---|---|
| Ingredient | Percent w/v |
| (-)erythro-α-methyl norepinephrine | 0.20 |
| Oxine sulfate 0.01 | |
| Sodium bisulfite | 0.3 |
| Boric acid | 0.8 |
| Sodium borate | 0.6 |
| Phenylmercuric acetate | 0.002 |
| Water, q.s. | |

As mentioned hereinabove, the compositions of this invention can also be formulated and administered as ophthalmic ointments compounded, for example, by mixing finely milled powdered ingredients with a small amount of white petrolatum and livigating or otherwise combining until a uniform distribution is achieved. The balance of white petrolatum is added by geometric addition until the desired dosage form is made.

The compositions of the present invention have been tested in standard laboratory animals and found to possess the capability of lowering mammalian intraocular pressure without substantial mydriasis. The effect of different concentrations of racemic α-methyl norepinephrine hydrochloride in 0.9 percent (w/v) physiological saline applied singly to one eye of conscious rabbits is summarized in Table I, below.

TABLE 1

The Ocular Response to a Single Topical Application of α-Methyl Norepinephrine to One Eye (Exp) of Conscious Rabbits

| Conc'n, Percent Wt. by Volume | Intraocular Pressure (mm Hg) | | | Pupil Diameter (mm) | | |
|---|---|---|---|---|---|---|
| | Control Eye | Exp. Eye | Mean Δ | Control Eye | Exp. Eye | Mean Δ |
| 0 | 21.2 ± 0.6 | 21.0 ± 0.6 | 0.2 ± 0.01 (10) | 3.4 ± 0.13 | 3.5 ± 0.18 | 0.05 ± 0.1 (10) |
| 0.1 | 21.4 ± 1.6 | 20.5 ± 1.3 | 0.9 ± 0.3 (4) | 3.7 ± 0.25 | 4.6 ± 0.47 | 0.9 ± 0.4 (4) |
| 0.3 | 21.0 ± 0.6 | 16.5 ± 0.3 | 4.5 ± 0.3 (4) | 3.1 ± 0.3 | 4.4 ± 0.9 | 1.2 ± 0.63 (4) |
| 0.5 | 21.5 ± 0.7 | 15.5 ± 0.8 | 6.0 ± 0.3 (4) | 3.0 ± 0.1 | 3.9 ± 0.4 | 0.9 ± 0.5 (4) |
| 0.8 | 22.5 ± 1.4 | 15.7 ± 1.1 | 6.8 ± 0.7 (6) | 3.7 ± 0.27 | 4.8 ± 0.42 | 1.1 ± 0.30 (6) |
| 1.0 | 21.6 ± 0.7 | 14.3 ± 0.6 | 7.4 ± 0.7 (10) | 3.7 ± 0.21 | 7.2 ± 0.51 | 3.4 ± 0.4 (10) |

The reported pressure and pupillary responses are the means of the maximal responses based on the time courses of the responses in pairs of eyes of individual rabbits. The number in parentheses () denotes the number of experimental subjects.

The mean time course of the ocular response to a 0.5 percent (w/v) solution of racemic α-methyl norepinephrine in 0.9 percent (w/v) physiological saline applied unilaterally to conscious rabbits is shown in Table II, below.

TABLE II

The Effect of a Single Application of 0.5 Percent (w/v) α-Methyl Norepinephrine on the Intraocular Pressure of Six Conscious Rabbits

| Time, hours | Intraocular Pressure (mm Hg) | | |
|---|---|---|---|
| | Control Eye | Treated Eye | Mean Δ Control - Exp. |
| 0 | 23.2 ± 1.3 (6) | 22.8 ± 1.4 (6) | 0.3 ± 0.3 (6) |
| 1 | 23.0 ± 1.6 (6) | 20.2 ± 1.6 (6) | 2.8 ± 0.9 (6) |
| 3 | 23.0 ± 1.3 (6) | 15.8 ± 1.3 (6) | 7.2 ± 0.9 (6) |
| 4 | 23.0 ± 1.4 (6) | 16.7 ± 1.2 (6) | 6.3 ± 1.2 (6) |

The drug was applied unilaterally (treated eye). In the third column is reported the mean pressure difference in pairs of eyes of individual rabbits. The number in parentheses denotes the number of experimental subjects.

Tables III A, IIIB, IV and V, below, summarize the experimental results using racemic α-methyl epinephrine, diester of α-methyl epinephrine, and diester of α-methyl norepinephrine in 0.9 percent (w/v) physiological saline. These results strikingly demonstrate the unexpected lack of pupillary dilation while reducing intraocular pressure. The observed lack of pupillary response is in marked contrast to the ocular response to dipivalyl ester of epinephrine as reported by Hussain et al. in U.S. Pat. No. 3,809,714.

TABLE III A

The Intraocular Pressure Response of Eight Conscious Rabbits to a Single Application of 0.5 Percent (w/v) Solution of α-methyl Epinephrine Hydrochloride

| Time, hours | Intraocular Pressure (mm Hg) | | |
|---|---|---|---|
| | Control Eye | Exp. Eye | Mean Δ Control - Exp. |
| 0 | 22.6 ± 0.8 | 22.7 ± 0.6 | −0.1 ± 0.2 |
| 0.5 | 22.8 ± 0.9 | 19.4 ± 1.3 | 3.3 ± 0.8 |
| 1.0 | 21.8 ± 1.0 | 15.9 ± 1.2 | 5.9 ± 0.6 |
| 3.0 | 20.1 ± 0.9 | 14.1 ± 0.5 | 6.0 ± 0.8 |
| 5.0 | 20.1 ± 0.7 | 14.6 ± 0.6 | 5.5 ± 0.7 |

TABLE III A-continued

The Intraocular Pressure Response of Eight Conscious Rabbits to a Single Application of 0.5 Percent (w/v) Solution of α-methyl Epinephrine Hydrochloride

| Time, hours | Intraocular Pressure (mm Hg) | | |
|---|---|---|---|
| | Control Eye | Exp. Eye | Mean Δ Control - Exp. |
| 24.0 | 23.5 ± 0.9 | 22.9 ± 0.9 | 0.6 ± 0.1 |

The drug was applied unilaterally (Exp. Eye) at T = 0 hr. In the third column is reported the mean pressure difference between pairs of eyes of individual rabbits.

TABLE III B

The Lack of Mydriatic Response in Eight Conscious Rabbits to a Single Application of 0.5 Percent (w/v) Solution of α-Methyl Epinephrine Hydrochloride

| Time, hours | Pupil Diameter (mm) | | |
|---|---|---|---|
| | Control Eye | Exp. Eye | Mean Δ Exp. - Control |
| 0 | 3.2 ± 0.1 | 3.1 ± 0.1 | −0.1 ± 0.1 |
| 0.25 | 3.2 ± 0.1 | 3.2 ± 0.1 | 0.0 ± 0.1 |
| 0.5 | 3.2 ± 0.2 | 3.2 ± 0.1 | 0.0 ± 0.1 |
| 1 | 3.2 ± 0.2 | 3.4 ± 0.1 | 0.2 ± 0.1 |
| 3 | 3.2 ± 0.2 | 3.1 ± 0.1 | −0.1 ± 0.1 |
| 5 | 3.2 ± 0.1 | 3.1 ± 0.1 | −0.1 ± 0.1 |

The active ingredient was applied unilaterally (Exp. eye) at T = 0 hr. In the third column is reported the mean pupil diameter differences in pairs of eyes. This data was taken on the same animals and during the same study as shown in Table III A, above.

TABLE IV

The Intraocular Pressure Response of Six Conscious Rabbits to a Single Application of 0.1 Percent (w/v) Solution of Dipivalyl Ester of α-Methyl Epinephrine

| Time, hours | Intraocular Pressure (mm Hg) | | |
|---|---|---|---|
| | Control Eye | Exp. Eye | Mean Δ Control - Exp. |
| 0 | 21.6 ± 0.5 | 21.7 ± 0.5 | −0.1 ± 0.1 |
| 1.0 | 21.8 ± 0.5 | 15.9 ± 1.0 | 5.9 ± 1.4 |
| 3.0 | 20.3 ± 0.5 | 12.8 ± 0.6 | 7.5 ± 0.7 |
| 5.0 | 19.9 ± 0.6 | 13.2 ± 0.6 | 6.7 ± 0.8 |
| 24.0 | 20.0 ± 0.6 | 18.4 ± 0.4 | 1.5 ± 0.3 |

The active ingredient was applied unilaterally (Exp. Eye) at T = 0 hr. In the third column is reported the mean pressure difference between pairs of eyes of individual rabbits.

TABLE V

The Intraocular Pressure Response of Four Conscious Rabbits to a Single Application of 0.1 Percent (w/v) Solution of Dipivalyl Ester of α-Methyl Norepinephrine

| Time, hours | Intraocular Pressure (mm Hg) | | Mean Δ Control - Exp. |
|---|---|---|---|
| | Control Eye | Exp. Eye | |
| 0 | 20.8 ± 0.7 | 20.5 ± 0.7 | 0.3 ± 0.1 |
| 1.0 | 21.3 ± 0.6 | 17.1 ± 0.4 | 4.2 ± 0.4 |
| 3.0 | 20.7 ± 0.8 | 11.8 ± 0.3 | 8.9 ± 1.1 |
| 5.0 | 20.4 ± 0.6 | 12.1 ± 0.3 | 8.4 ± 0.8 |
| 24.0 | 20.8 ± 0.4 | 18.3 ± 0.4 | 2.5 ± 0.2 |

The active ingredient was applied unilaterally (Exp. Eye). In the third column is reported the mean pressure difference between pairs of eyes of individual rabbits.

The unexpected nature of the present invention is further illustrated in the FIGURE by the dose response curves for α-methyl derivatives of norepinephrine and epinephrine as compared to the dose response curves for epinephrine and norepinephrine. Data for the foregoing curves were obtained by applying a solution of the compound in 0.9 percent (w/v) physiological saline to eyes of individual rabbits.

I claim:

1. A method of treating ocular hypertension in a mammal which comprises topically applying to the eye of the mammal in need of such treatment an effective intraocular pressure-reducing amount, but less than an amount inducing substantial mydriasis, of a catecholamine of the general formula

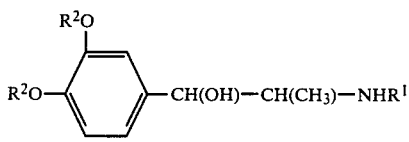

wherein $R^1$ is a member of the group consisting of hydrogen and methyl, and $R^2$ is a member of the group consisting of hydrogen and acyl containing 1 to 8 carbon atoms, inclusive, or the pharmacologically acceptable acid addition salt thereof, together with an ophthalmic vehicle.

2. The method in accordance with claim 1 wherein the applied amount of said catecholamine is about 0.01 to about 5 milligrams and the concentration of the catecholamine in said ophthalmic vehicle is no more than about 0.5 percent, weight by volume.

3. The method in accordance with claim 1 wherein the applied amount of said catecholamine is about 0.02 to about 2 milligrams and the concentration of the catecholamine in said ophthalmic vehicle is about 0.001 to about 0.15 percent, weight by volume.

4. The method in accordance with claim 1 wherein the catecholamine is α-methyl epinephrine.

5. The method in accordance with claim 1 wherein the catecholamine is (−)erythro-α-methyl epinephrine.

6. The method in accordance with claim 1 wherein the catecholamine is an acid addition salt of α-methyl epinephrine.

7. The method in accordance with claim 6 wherein the catecholamine is α-methyl epinephrine hydrochloride.

8. The method in accordance with claim 1 wherein the catecholamine is α-methyl epinephrine ascorbate.

9. The method in accordance with claim 1 wherein the catecholamine is (−)erythro-α-methyl epinephrine hydrochloride.

10. The method in accordance with claim 1 wherein the catecholamine is (−)erythro-α-methyl epinephrine ascorbate.

11. The method in accordance with claim 1 wherein the catechloramine is α-methyl norepinephrine.

12. The method in accordance with claim 1 wherein the catecholamine is (−)erythro-α-methyl norepinephrine.

13. The method in accordance with claim 1 wherein the catecholamine is an acid addition salt of α-methyl norepinephrine.

14. The method in accordance with claim 13 wherein the catecholamine is α-methyl norepinephrine hydrochloride.

15. The method in accordance with claim 1 wherein the catecholamine is α-methyl norepinephrine ascorbate.

16. The method in accordance with claim 1 wherein the catecholamine is acylate.

17. The method in accordance with claim 16 wherein the acylate is α-methyl epinephrine dipivalate.

18. The method in accordance with claim 16 wherein the acylate is α-methyl norepinephrine dipivalate.

* * * * *